United States Patent
Henzler

(10) Patent No.: US 6,551,240 B2
(45) Date of Patent: Apr. 22, 2003

(54) ENDOSCOPE

(76) Inventor: Marc U. Henzler, Wilhelmstrasse 10, 78532 Tulingen (DE)

( * ) Notice: Subject to any disclaimer, the term of this patent is extended or adjusted under 35 U.S.C. 154(b) by 0 days.

(21) Appl. No.: 10/010,523

(22) Filed: Dec. 7, 2001

(65) Prior Publication Data

US 2002/0143239 A1 Oct. 3, 2002

(30) Foreign Application Priority Data

Dec. 7, 2000 (DE) .......................... 100 61 107

(51) Int. Cl.$^7$ ................................. A61B 1/06
(52) U.S. Cl. .................. 600/179; 348/68; 362/545; 362/574
(58) Field of Search ................. 600/178, 173; 362/545, 574; 398/68–70

(56) References Cited

U.S. PATENT DOCUMENTS 6,331,156 B1 * 12/2001 Haefele et al. ............. 600/179
6,449,006 B1 * 9/2002 Shipp .......................... 348/70

FOREIGN PATENT DOCUMENTS

DE        296 13 103 U1  *  11/1997  ............ A61B/1/06
GB        2357856 A       *  7/2001   ............ G02B/23/26

* cited by examiner

Primary Examiner—John Mulcahy
(74) Attorney, Agent, or Firm—Pendorf & Cutliff

(57) ABSTRACT

An endoscope is described, in which a shaft is included with inner and outer sheath pipes (1, 2) multiple illumination units (10) with LED's (25) provided for producing illumination light cascade-like, axially sequentially. The illumination units (10) consist of light transmissive carriers, upon which the LED's (25) are bonded. The light produced by the sequentially arranged illumination units (10) is emitted at the distal end with a high intensity of illumination, preferably after reflection from a mirror (11) provided at the proximal end.

24 Claims, 3 Drawing Sheets

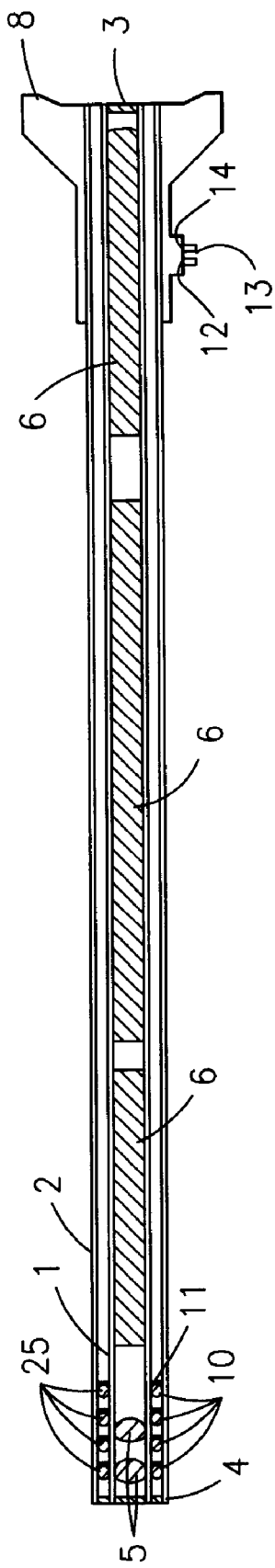
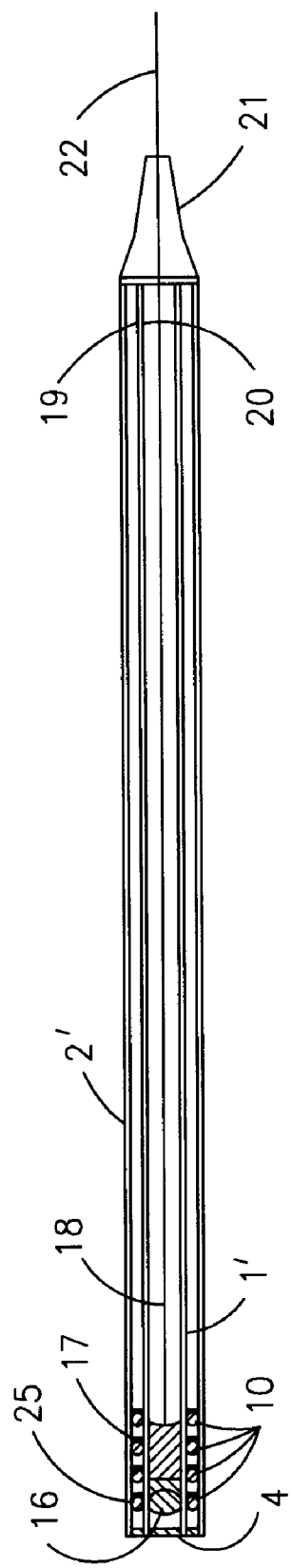
Fig. 1
Fig. 2

ENDOSCOPE

BACKGROUND OF THE INVENTION

1. Field of the Invention

With this type of endoscope it is possible to carry out for example minimal invasive therapeutic or diagnostic interventions. It is also possible to employ this endoscope for example in technical endoscopy as a so called technoscope.

2. Description of the Related Art

These endoscopes include a shaft to be introduced into a hollow space, on the proximal end of which the image is projected by means of a special optical system, preferably a rod lens system, onto a lens situated in an eyepiece. The image of the area of operation or the hollow space to be viewed produced in this manner is displayed on a monitor by means of an associated camera or a signal divider and control unit (camera controller).

Generally the illumination light is conducted from an external light source along a light guide comprised of a fiber bundle or a liquid guide to the endoscope, and from is coupled to additional light guides provided in the inside of the endoscope, which internal light guides conduct light to the distal end of the endoscope.

This conventional illumination system is technically complex. The conventionally employed cold light sources, for example xenon- or halogen lights, require a relatively high electrical power and require technically complex measures for wiring and for cooling, in order to supply sufficient light to the distal end of the endoscope even in the case of long light guides and high transmission or coupling losses. Also, the above mentioned light sources do not have an optimal efficiency.

In addition there is a high failure rate due to the short life span of these light sources and the high mechanical stresses to which the light bundles are subjected, which results in high maintenance costs and therewith a reduction in the economic justifiability.

From DE 296 13 103 U1, DE 298 12 048 U1 endoscopes are known in which light emitting diodes, so called LED's, are provided at the distal end of the endoscope as the illumination source.

The advantage of providing the illumination source at the distal end is that coupling losses between the light guides and transmission losses through the long light guides can be avoided. Further, a CCD-Chip (Charge Coupled Device-Chip) can be provided at the distal end of the endoscope as image receiver, whereby image light intensity losses consequent to air or glass transmission can be avoided.

In DE 296 13 103. U1 the use of LED-Chips is proposed for the representation of the colors red, blue and green to take advantage of the fluorescence excitation produced by fluorescent materials which collect in carcinogenic tissue. This use makes it necessary to use a chip with CCD-elements for black-white transmission, wherein a dichroic filter with a transmissivity of >56 nm must be interposed. This arrangement, in particular the use of the mentioned black-white-CCD, however, substantially reduces the possible areas of employment of the endoscope.

In DE 299 10 795 U1 an endoscope is described, in which multiple illumination units are provided axially sequentially on the shaft, wherein light is supplied through light guides via arrays of LED's situated at the proximal end. This arrangement requires greater amounts of energy, due to the increased amount of light produced by the greater number of illumination units employed in the total system and the losses due to the coupling in of the individual illumination units in the light guides. Besides this, the coupling in of the light guides and their incorporation in a shaft is complex in thus very expansive.

SUMMARY OF THE INVENTION

The present invention is based on the task of providing an endoscope in which the operation and ergonomics are improved and with which the manufacturing costs are reduced through the improvement in the integration of the illumination system. Besides this the outer diameter of the endoscope shaft should be as small as possible.

It is the basic idea of the invention to use, as illumination devices, LED's on ring shaped, light transmissive carriers, in the following also referred to as illumination rings, which are provided between the inner and outer sheath tube, that is, surrounding the optics, wherein multiple carriers are provided axially, cascade-like, sequentially between the proximal and distal end of the shaft in the ring space between inner and outer sheath pipe.

With an arrangement of this type a substantially greater light density is produced than with known endoscopes of this type. Glass fiber light guides in the inside of the shaft pipe can be completely dispensed with.

Thereby the manufacturing is simplified and costs are reduced, and a very narrow shaft diameter can be realized.

The LED's forming the illumination units can be bonded to carriers in the form of ring-shaped glass discs, that is, mechanically wired, and the conductor circuits for supplying current to the LED's can be produced by vapor deposition, preferably gold vapor deposition. Thereby a significantly greater manufacturing density achieved, which cannot be achieved with conventional premanufactured LED's or with SMD LED's (Surface Mounted Device-LED's).

A further increase in the light density can be achieved thereby, that a mirror reflecting the light is provided behind the proximal last carrier, which can be comprised of a vapor deposited metal layer. The idea serves the same purpose, wherein the opposing or facing surfaces of the inner and outer sheath pipe, between which the carrier with the LED's is provided, is entirely or partially provided with a reflective layer.

In known manner the distal end of the shaft is closed of with a light transmissive plate or even with a lens.

Further means for economical production of the carrier for the light units are set forth.

The supply of current for the LED's can occur, via an electrical supply circuit, which extends in the ring space between inner and outer hollow space, and which is electrically connected via a plug-in contact. In this plug-in contact a plug adapted for supplying current can be plugged in. Thereby the endoscope can be connected and disconnected in a very simple manner.

A contactless current supply for the LED's is possible, when the electrical supply lines are connected with a induction coil provided in the lens or optics. Current can be produced in this coil by a contactless surrounding, magnetic field producing induction coil, which current is supply to the LED's.

By this means the manipulability, and above all the ability to clean, in particular the ability to sterilize in an autoclave, are further improved.

Alternatively, in a parallel wiring of the LED's the sheath pipe can also be employed as conductor. In the case of soldering the light rings with the sheath pipe, this can be used to advantage for conducting away heat.

By dispensing with external light sources, as well as the light cable connecting these with the endoscope, the manufacturing and maintenance costs of this type of system are reduced. Supply costs for light cables and gas discharge lamps are dispensed with, the need for repairs is reduced, which results in a very high reliability of the system.

Besides white emitting LED's, monochromatic emitting LED's can be employed. In this case, by wave convection by means of the red, green and blue light emitted by the LED's white light can be produced, in that the complementary colors are mixed in a particular relationship.

Means for image reproduction are set forth.

BRIEF DESCRIPTION OF THE DRAWINGS

The subject matter of the invention will be described in the following on the basis of the illustrative embodiments shown in the figures. In the figures there is shown FIG. 1 longitudinal section of an endoscope according to a first embodiment of the invention in schematic representation, wherein light rings are provided in the shaft pipe, FIG. 2 longitudinal section of a shaft pipe according to a second embodiment in schematic representation, wherein light rings and a CCD as opto-electric image producing device are provided, FIG. 3 perspective representation of an individual light ring according to the invention, and FIG. 4 schematic diagram of an arrangement with the inventive endoscope and viewing device.

DETAILED DESCRIPTION OF THE INVENTION

Figure 3:
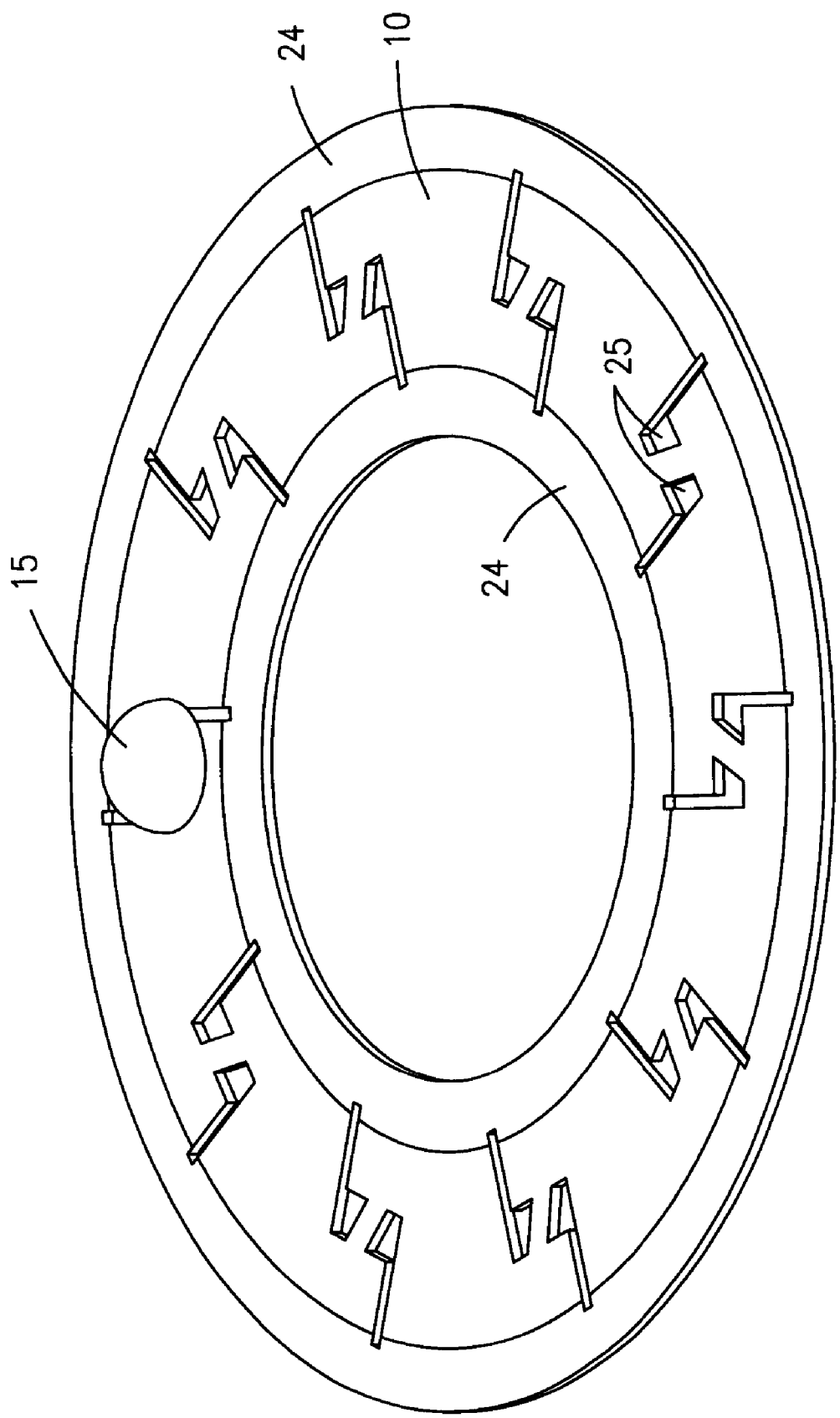

FIG. 1 shows in schematic representation an endoscope designed in accordance with a first embodiment of the invention.

This endoscope is essentially comprised of a shaft with inner sheath pipe 1 and outer sheath pipe 2, on the proximal end of which an ocular or lens plate 8 is provided and of which the distal end is closed off liquid-tight with a glass closure plate 4. In the inner sheath pipe 1 a lens system 5 is provided comprised of two lenses. The image produced thereby is projected, via the rod lens system 6 provided on the inside of the sheath pipe 1, onto the glass closure plate 3 situated in the ocular 8, where it can be viewed by the user or be monitored via a camera.

At a distal end between inner and outer sheath pipe 1 and 2 are axial sequential light rings, namely, transparent carrier rings 10 with light diodes 25 bonded axially sequentially thereupon. The back side of the light ring relative closest to the ocular 8 is provided with a reflecting means 11. Thereby the light produced by the light diodes 25 of all light rings is directed to the distal end, where it can be emitted through the distal closure plate 4. For a further improved idealization of the light the facing inner surfaces of the inner and outer sheath pipe 1 and 2 in the area of the light rings 10 can be mirrored.

The light diodes 25 provided on the ring shaped carriers 10 are preferably connected in parallel, as can be seen from the representation according to FIG. 3. There electrical connections are in the form of pad layers 24. Therewith the current supply to the LED's 25 can occur through the sheath pipes 1 and 2, which are connected via connecting conductors 12 or 14 with an electrical plug-in connector 13 provided at the ocular plate 8.

In the second embodiment, according to FIG. 2 there is provided on the distal end of the shaft pipe, namely within the inner shaft pipe 1', an opto-electrical image producing unit 17, which has on the distal side a collecting lens 16. Further, also in this embodiment the above described light rings 10 are provided at the distal end. The image signals produced by the opto-electrical image unit 17 are conveyed via the central signal transmitter 18, which ends at the closure cap 21, and are supplied via the external connecting cable 22 to the not-shown monitor.

The current supply to the light diodes 25 provided on the light rings 10 occurs in the same manner as in the embodiment according to FIG. 1 via inner and outer sheath pipes 1' and 2'. These holow pipes are connected at the proximal end with the external connector cable 22 via conductors 19 and 20.

In FIG. 3 a perspective view of an individual light ring is shown. The light ring is comprised of a carrier 10 of glass, upon which a plurality of light diodes, which are formed of cathodes and anodes 25. The cathodes and anodes 25 of these light diodes are covered over with a transparent adhesive, a so-called bubble. As bubble material one could employ epoxy resin, urethane acrylate or silicone. These materials can be laced with a fluorescent material, whereby the blue light emitted by the LED is converted to a white light, which technique is known under the name luminescence wavelength conversion. With this UBH-LED (Ultra-High-Bright) as light source an emitting range can be achieved which represents the complete spectrum of white light which is visible to the human eye.

The current supply for the diodes occurs via ring-shaped pads 24, which in the assembled condition are in electrical contact with the inner and outer sheath pipes 1 and 2, preferably soldered.

Figure 4:
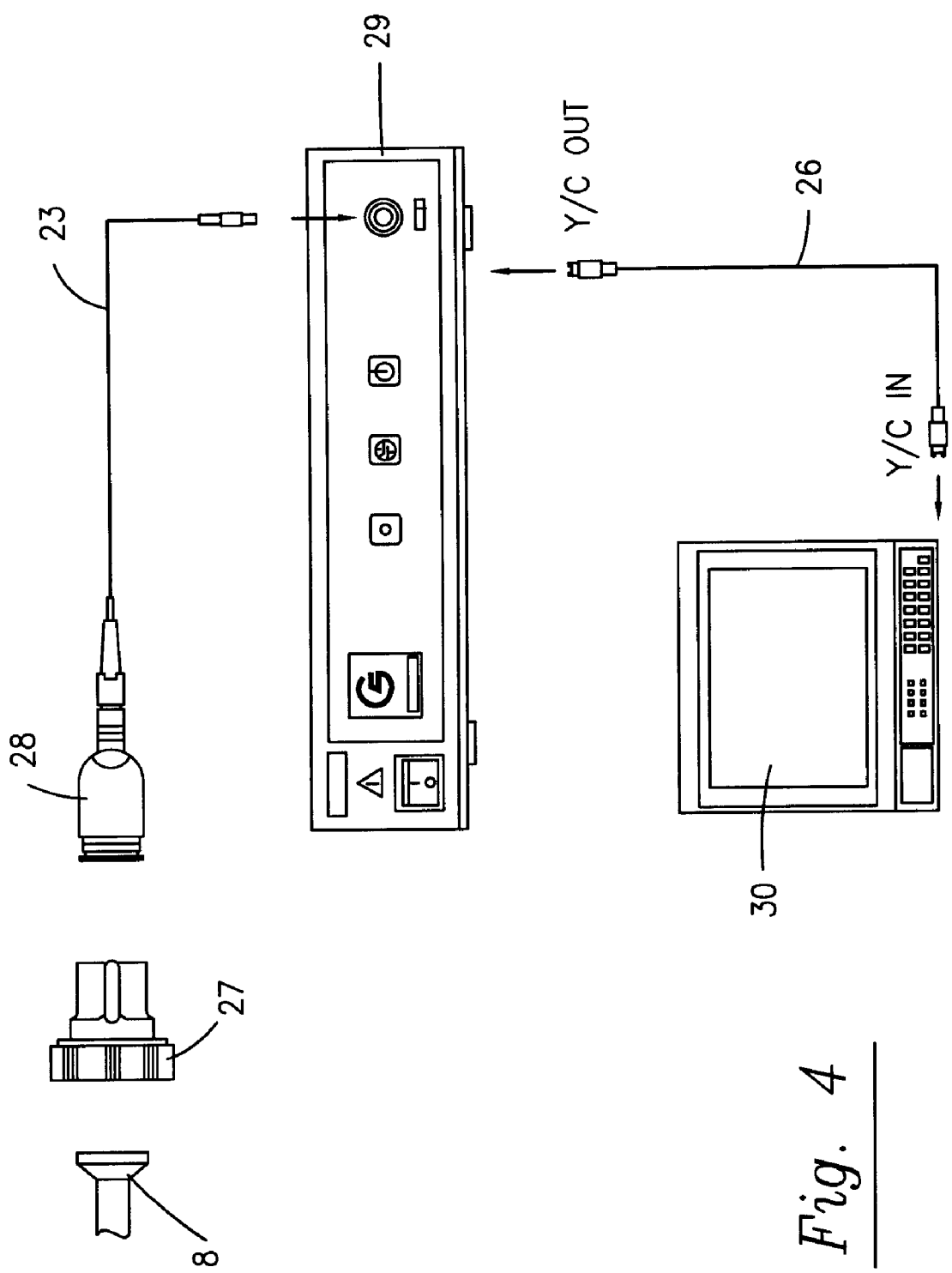

The schematic diagram according to FIG. 4 shows one possible setup of the inventive endoscope, of which endoscope here essentially only the ocular 8 is shown. In this ocular 8 a lens 27 can be clamped. To this lens 27 a camera head 28 can be connected. The signals recorded by the camera head 28 are supplied via the connecting cable 23 to the control unit 29, where they can be processed for producing the monitor signals. Thereby the image produced by the endoscope can be viewed with a monitor 30 which is connected via the cable 26 to the control unit 29.

REFERENCE NUMBER LIST 1 inner sheath pipe of the shaft
2 outer sheath pipe of the shaft
3 proximal connection plate of glass in the ocular 8
4 distal closure plate
5 lens system
6 rod lens system
7 - - -
8 ocular
9 - - -
10 ring shaped carrier
11 mirror
12 connecting conductor between inner sheath pipe 1 and plug-in contact 13
13 plug contact
14 connecting conductor between outer sheath pipe 2 and plug-in contact 13
15 bubble
16 collecting lens 17 opto-electric image producing unit
18 signal transmitter
19 connecting conductor between inner sheath pipe 1' and connecting cable 22
20 connecting conductor between outer sheath pipe 2' and connecting cable 22
21 closure cap
22 attachment cable
23 connecting cable between camera head 28 and control unit 29
24 pad layer as contact ring
25 light emitting diode (LED) comprised of cathode and anode
26 connecting cable between control unit 29 and monitor 30
27 lens with clamp device for the lens plate 8
28 camera head
29 control unit
30 monitor

What is claimed is:

1. An endoscope comprising:

a shaft with coaxial outer and inner sheath pipes (1, 2);

an optic system provided in the inner sheath pipe (2);

a lens system (5) provided at the distal end; and illumination units (10) provided in the shaft with ring-like light emitting diodes (25) (LED's) surrounding the inner sheath pipe (2) for producing the light of illumination, wherein the LED's (25) are provided on ring-shaped light-transmissive carriers (10), which carriers (10) are provided between the inner and outer sheath pipes (1, 2), and wherein multiple carriers (10) are provided between the proximal and distal ends of the shaft in the ring space between the inner and outer sheath pipes (1, 2) cascade-like, axially sequentially.

2. An endoscope according to claim 1, wherein said optic system is a rod lens system (6).

3. An endoscope according to claim 1, wherein said lens system (5) is a collecting lens (16).

4. An endoscope according to claim 1, wherein the carriers (10) are ring shaped glass plates, upon which the LED's (25) are bonded and to which conductive circuits (24) for supplying current to the LED's (25) are provided by vapor deposition of the glass plates (10).

5. An endoscope according to claim 4, wherein the conductive circuits are provided by gold vapor deposition.

6. An endoscope according to claim 1, wherein the most proximal carrier is provided with a reflector (11) on the proximal side.

7. An endoscope according to claim 6, wherein the reflector (11) is comprised of a metal layer, vapor deposited upon the carrier (10).

8. An endoscope according to claim 1, wherein the facing surfaces of the inner and outer sheath pipe (1, 2) are completely or partially provided with reflective layers.

9. An endoscope according to claim 8, wherein reflective layers have a high mirror finish.

10. An endoscope according to claim 1, wherein a light transmissive closure plate (4) is provided at the distal end of the shaft.

11. An endoscope according to claim 1, wherein the carriers (10) for provision of pads are layered with a metal alloy.

12. An endoscope according to claim 11, wherein the metal alloy is a nickel-gold alloy.

13. An endoscope according to claim 11, wherein on the carriers (10) with the pads (24), a wafer containing the LED's is provided using a bonding process.

14. An endoscope according to claim 13, wherein the LED's (25) are covered with bubbles (15).

15. An endoscope according to claim 14, wherein the bubble material is selected from the group consisting of epoxy resin, urethane acrylate and silicone.

16. An endoscope according to claim 15, wherein said bubble material is laced with a fluorescing material.

17. An endoscope according to claim 1, wherein electrical supply lines for the LED's (25) extend in the ring space between inner and outer sheath pipes (1, 2) and are connected to a plug-in contact (13) provided at an ocular or lens (8), which is adapted to receive a current supplying plug.

18. An endoscope according to claim 17, wherein the LED's (25) are connected electrically in parallel and that the current supply occurs via the inner and outer sheath pipes (1, 2), wherein conductive lines provided on the carriers (10) are electrically conductively connected with the sheath pipes (1, 2).

19. An endoscope according to claim 18, wherein the carriers (10) are pad deposition or lamination layers (24), and wherein the electrical connection with the sheath pipes (1, 2) is a soldered connection.

20. An endoscope according to claim 1, wherein electrical supply lines for the LED's extend in the ring space between inner and outer sheath pipes (1, 2) and are connected with a secondary contactless induction coil provided in an ocular, which is associated with a magnetic field producing primary induction coil which surrounds the secondary contactless induction coil.

21. An endoscope according to claim 20, wherein the LED's (25) are connected electrically in parallel and that the current supply occurs via the inner and outer sheath pipe (1, 2), wherein conductive lines provided on the carriers (10) are electrically conductively connected with the sheath pipes (1, 2).

22. An endoscope according to claim 1, wherein said LEDs are white emitting or monochromatic emitting LED's (25).

23. An endoscope according to claim 1, wherein the ocular plate (8) is associated with a camera head (28), which is connected with a monitor (30) via a control unit (29).

24. An endoscope according to claim 1, wherein an opto-electrical image producing unit (17) is integrated in the shaft, which is connected with a monitor via a control unit.

* * * * *